United States Patent [19]

Lukas-Laskey et al.

[11] Patent Number: 5,760,069
[45] Date of Patent: Jun. 2, 1998

[54] METHOD OF TREATMENT FOR DECREASING MORTALITY RESULTING FROM CONGESTIVE HEART FAILURE

[75] Inventors: Mary Ann Lukas-Laskey. Philadelphia; Robert Ruffolo, Jr., Spring City; Neil Howard Shusterman, Wynnewood, all of Pa.; Gisbert Sponer, Laudenbach; Klaus Strein, Hemsbach, both of Germany

[73] Assignee: Boehringer Mannheim Pharmaceuticals Corporation-SmithKline Beecham Corporation Limited Partnership #1, Rockville, Md.

[21] Appl. No.: 483,635

[22] Filed: Jun. 7, 1995

[51] Int. Cl.$^6$ .......................... A61K 31/40; A61K 31/54; A61K 31/34; A61K 31/585
[52] U.S. Cl. .................. 514/411; 514/423; 514/223.2; 514/223.5; 514/471; 514/175
[58] Field of Search .................................. 514/411, 423, 514/223.2, 223.5, 471, 175

[56] References Cited

U.S. PATENT DOCUMENTS

| | | | |
|---|---|---|---|
| 4,888,179 | 12/1989 | Appelgren et al. | 424/480 |
| 5,308,862 | 5/1994 | Ohlstein | 514/411 |
| 5,312,828 | 5/1994 | Finkelstein et al. | 514/381 |

OTHER PUBLICATIONS

J. of Cardiovascular Pharm; Senior, et al., "Effects of Carvedilol on Ventricular Arrhythmias", 1992, vol. 19, (Suppl. 1): pp. S117–S121.

J. of Cardiovascular Pharm; DasGupta, et al., "The Effects of Intravenous Caredilol, A New Multiple Action Vasodilatory β–Blocker, in Cogestive Heart Failure", 1991, vol. 18, (Suppl. 1): pp. S12–S16.

British J. of Urology; Caine, et al., "The Use of Alpha-adrenergic Blockers in Benign Prostatic Obstruction", 1976, vol. 48, pp. 255–263.

British J. of Urology; H.N. Whitfield, et al., "The Effect of Adrenergic Blocking Drugs on Outflow Resistance", 1976, vol. 47, pp. 823–827.

American J. of Cardiology; DasGupta, et al., "Value of Carvedilol in Congestive Heart Failure Secondary to Coronary Artery Disease", 1990, vol. 66, pp. 1118–1123.

Z. Kardiol; A. Buchwald, et al., "Acute Hemodynamic Effects of the Beta–blocker Carvedilol in Heart Failure", 1990, vol. 79, No. 6, pp. 424–428.

JACC; DiLenarda, et al., "Acute Hemodynamic Effects of Carvedilol Versus Metoprolol In Idiopathic Dilated Cardiomyopathy", 1991, vol. 17, No. 2, Abstract 142A.

Frontiers in CHF; D. Tepper, "Multicenter Oral Carvedilol Heart Failure Assessment", 1996, vol. 2. No. 1, pp. 39–40.

J. of Cardiovascular Pharm; DasGupta, et al., 1990, vol. 19, (Suppl. 1): pp. 562–567.

J. of Hypertension, C. Rosendorff, "Beta–blocking agents with vasodilator activity", 1993, vol. 11, (Suppl. 4): pp. S37–S40.

Cardiology; J. Lessem, et al., "Development of a Multication Beta–blocker", 1993, vol. 82, (Suppl. 3): pp. 50–58.

Drug Safety; W.J. Louis, et al., "A Risk–Benefit Assessment of Carvedilol in the Treatment of Cardiovascular Disorders, ", 1994, vol. 11, No. 2, pp. 86–93.

Drugs; McTavish, et al., "Carvedilol—A Review of its Pharmacodynamic and Pharmacokinetic Properties, and Therepeutic Efficacy", 1993, vol. 45, No. 2, pp. 232–258.

Circulation; H. Krum, et al., "Effects of Cavedilol, a Vasodilator-β-Blocker, in Patients with Congestive Heart Failure Due to Ischemic Heart Disease", 1995, vol. 92, No. 2, pp. 212–218.

CBS-TV; CBS Evenings News, Transcript, Jan. 27, 1993, 6:30-7:00pm.

CNBC; Steals and Deals, Transcript, Jan. 29, 1993, 8:30pm.

Circulation, DasGupta, et al., 1989, vol. 80, No. 4, (Suppl. II): pp. 116–117.

Drugs of Today; Ruffolo, et al., "Carvedilol (Kredex): A Novel Multiple Action Cadiovascular Agent", 1991, vol. 27, No. 7, pp. 465–492.

*Primary Examiner*—William R. A. Jarvis
*Attorney, Agent, or Firm*—Mary E. McCarthy; Stephen Venetianer; Edward T. Lentz

[57] ABSTRACT

A method of treatment using a compound of Formula I:

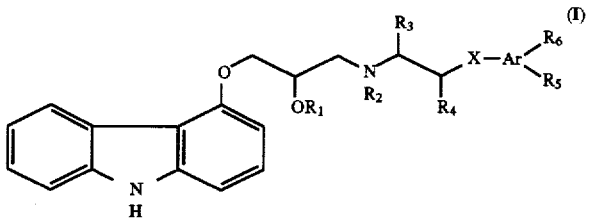

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

or a pharmaceutically acceptable salt thereof, alone or in conjunction with one or more other therapeutic agents, said agents being selected from the group consisting of ACE inhibitors, diuretics, and digoxin for decreasing mortality resulting from congestive heart failure (CHF) in mammals, particularly humans.

7 Claims, No Drawings

METHOD OF TREATMENT FOR DECREASING MORTALITY RESULTING FROM CONGESTIVE HEART FAILURE

FIELD OF THE INVENTION

The present invention relates to a new method of treatment using compounds which are dual non-selective β-adrenoceptor and α₁-adrenoceptor antagonists, in particular the carbazolyl-(4)-oxypropanolamine compounds of Formula I, preferably carvedilol, for decreasing the mortality of patients suffering from congestive heart failure (CHF). The invention also relates to a method of treatment using compounds which are dual non-selective β-adrenoceptor and α₁-adrenoceptor antagonists, in particular the carbazolyl-(4)-oxypropanolamine compounds of Formula I, preferably carvedilol, in conjunction with one or more other therapeutic agents, said agents being selected from the group consisting of angiotensin converting enzyme (ACE) inhibitors, diuretics, and digoxin, for decreasing the mortality of patients suffering from CHF.

BACKGROUND OF THE INVENTION

Congestive heart failure occurs as a result of impaired pumping capability of the heart and is associated with abnormal retention of water and sodium. Traditionally, treatment of chronic mild failure has included limitation of physical activity, restriction of salt intake, and the use of a diuretic. If these measures are not sufficient, digoxin, which is an agent that increases the force of mycardial contraction, is typically added to the treatment regiment. Subsequently, angiotensin converting enzyme inhibitors, which are compounds that prevent the conversion of angiotensin I into the pressor-active angiotensin II, are prescribed for chronic treatment of congestive heart failure, in conjunction with a diuretic, digoxin, or both.

Congestive heart failure is a condition that is associated with activation of both the renin-angiotensin system (RAS) and the sympathetic nervous system (SNS). Modulation of the RAS by angiotensin converting enzyme inhibitors has been shown to improve the symptoms associated with CHF. Sharpe, D. N., Murphy, J., Coxon, R. & Hannan S. F. (1984) *Circulation*, 70, 271–278. However, ACE inhibitors appear to have little effect on the enhanced SNS in CHF. Cohn, J. N., Johnson, G. & Ziesche, S., (1991) *N. Engl. J. Med.*, 325, 293–302 and Francis, G. S., Rector, T. S. & Cohn, J. N. (1988) *Am. Heart J.*, 116, 1464–1468. Therefore, there is a need for an agent that would be effective in blocking the activation of the SNS in CHF patients.

Also, congestive heart failure is a well-known cardiac disorder which results in an annual mortality in excess of 50 percent. Applefeld, M. M., (1986) *Am. J. Med.*, 80, Suppl. 2B, 73–77. Therefore, therapeutic agents that would decrease the mortality resulting from CHF in patients suffering therefrom are highly desirable.

SUMMARY OF THE INVENTION

The present invention provides a new method of treatment using pharmaceutical compounds which are dual non-selective β-adrenoceptor and α₁-adrenoceptor antagonists and, in particular, the carbazolyl-(4)-oxypropanolamine compounds of Formula I, alone or in conjunction with one or more other therapeutic agents, said agents being selected from the group consisting of ACE inhibitors, diuretics, and digoxin, as therapeutics for decreasing mortality resulting from congestive heart failure in mammals, particularly humans. In particular, the present invention preferably provides a method of treatment, alone or in conjunction with one or more other therapeutic agents, said agents being selected from the group consisting of ACE inhibitors, diuretics, and digoxin, for the compound of Formula I wherein $R_1$ is —H, $R_2$ is —H, $R_3$ is —H, $R_4$ is —H, X is O, Ar is phenyl, $R_5$ is ortho —$OCH_3$, and $R_6$ is —H, said compound being better known as carvedilol, which is (1-(carbazol-4-yloxy-3-[[2-(o-methoxyphenoxy)ethyl]amino]-2-propanol), or a pharmaceutically acceptable salt thereof.

DETAILED DESCRIPTION OF THE INVENTION

U.S. Pat. No. 4,503,067 discloses carbazolyl-(4)-oxypropanolamine compounds of Formula I:

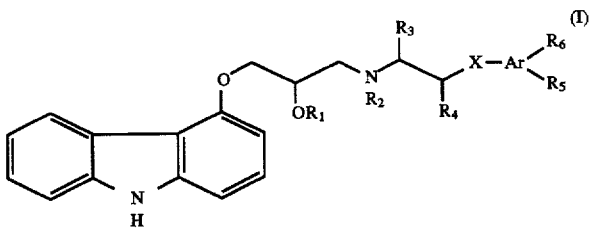

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

This patent further discloses a compound of Formula I, better known as carvedilol, which is (1-(carbazol-4-yloxy-3-[[2-(o-methoxyphenoxy)ethyl]amino]-2-propanol), having the structure shown in Formula II:

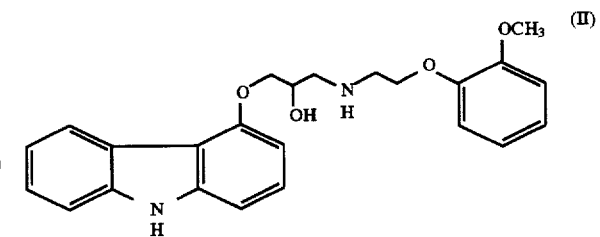

Formula I compounds, of which carvedilol is exemplary, are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $\alpha_1$-adrenoceptor blockade, whereas the $\beta$-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) *Eur. J. Pharmacol.*, 176,237–240; Nichols, A. J., Gellai, M. & Ruffolo, R. R., Jr. (1991) *Fundam. Clin. Pharmacol.*, 5, 25–38; Ruffolo, R. R., Jr., Gellai, M., Hieble, J. P., Willette, R. N. & Nichols, A. J. (1990) *Eur. J. Clin. Pharmacol.*, 38, S82-S88; Ruffolo, R. R., Jr., Boyle, D. A., Venuti, R. P. & Lukas, M. A. (1991) *Drugs of Today*, 27, 465–492; and Yue, T.-L., Cheng, H., Lysko, P. G., Mckenna, P. J., Feuerstein, R., Gu, J., Lysko, K. A., Davis, L. L. & Feuerstein, G. (1992) *J. Pharmacol. Exp. Ther.*, 263,92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble, J. P., Willette, R. N. & Nichols, A. J. (1990) *Eur. J. Clin. Pharmacol.*, 38, S82-S88.. Carvedilol also markedly reduces infarct size in rat, canine and porcine models of acute myocardial infarction. Ruffolo, R. R., Jr., et al., *Drugs of Today*, supra, possibly as a consequence of its antioxidant action in attenuating oxygen free radical-initiated lipid peroxidation. Yue, T.-L., et al. supra.

Recently, it has been discovered in clinical studies that pharmaceutical compounds which are dual non-selective $\beta$-adrenoceptor and $\alpha_1$-adrenoceptor antagonists, in particular the compounds of Formula I, preferably carvedilol, alone or in conjunction with conventional agents, said agents being ACE inhibitors, diuretics, and digoxin, are effective therapeutic agents for treating CHF. The use of agents, such as carvedilol in treating CHF is surprising, since, in general, $\beta$-blockers are contraindicated in patients suffering from heart failure, because $\beta$-blockers are known to have undesirable cardiodepressive effects. The most surprising observation from the studies in which the instant compounds were used to treat CHF is that said compounds, in particular carvedilol, are able to decrease the mortality resulting from CHF in humans by about 67 percent. Furthermore, this result is present across all classifications of CHF and both etiologies (eschemic and non-eschemic). This result is surprising since two recent mortality studies using the $\beta$-blockers metoprolol (Waagstein, et al., (1993) *Lancet*, 342, 1441–1446) and bisoprolol (CIBIS investigators and committees, (1994) *Circulation*, 90, 1765–1773) in the treatment of CHF showed no difference in mortality between drug-treated patients and placebo-treated patients.

According to the method of treatment of the present invention, the desirable therapeutic effect of the compounds of Formula I, particularly carvedilol, may be augmented by using any one of said compounds, or any pharmaceutically acceptable salt of said compounds, in conjunction with ACE inhibitors, diuretics, and digoxin, which are effective therapeutic agents for the treatment of CHF. In particular, the preferred ACE inhibitors of the present invention are selected from the group consisting of captopril, lisinopril, and enalapril, or any pharmaceutically acceptable salts thereof and the preferred diuretics of the present invention are hydrochlorothiazide or furosemide, or any pharmaceutically acceptable salts thereof. The desireable therapeutic benefits of the compounds of Formula I, particularly carvedilol, are additive with those of such ACE inhibitors, or diuretics, or digoxin when administered in combination therewith. Captopril is commercially available from E. R. Squibb & Sons, Inc. Lisinopril, enalapril and hydrochlorothiazide are commercially available from Merck & Co. Furosemide is commercially available from Hoechst-Roussel Pharmaceuticals, Inc. Digoxin is commercially available from Burroughs Wellcome Co.

Compounds of Formula I may be conveniently prepared as described in U.S. Pat. No. 4,503,067. Carvedilol is commercially available from SmithKline Beecham Corporation and Boehringer Mannheim GmbH (Germany).

Pharmaceutical compositions of the compounds of Formula I, including carvedilol, alone or in combination with ACE inhibitors, or diuretics, or digoxin may be administered to patients according to the present invention in any medically acceptable manner, preferably orally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitered for well-known symptoms of intolerance, e.g., fainting, to such compound. Once the patient is found to tolerate such compound, the patient should be brought slowly and incrementally up to the maintenance dose. The preferred course of treatment is to start the patient on a dosage regimen of either 3.125 or 6.25 mg, preferably given twice daily, for two weeks. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for two more weeks, and observed for signs of intolerance. This course is continued until the patient is brought to a maintenance dose. The preferred maintenance dose is 25 mg, preferably given twice daily, for patients having a body weight of up to 85 kg. For patients having a body weight of over 85 kg, the maintenance dose is between about 25 mg and about 50 mg, preferably given twice daily; preferably about 50 mg, preferably given twice daily.

Dosing in humans for the treatment of disease according to the present invention includes the combination of compounds of Formula I with conventional agents. For example, the usual adult dosage of hydrochlorothiazide is 25–100 mg daily as a single dose or divided dose. The recommended starting dose for enalapril is 2.5 mg administered once or twice daily. The usual therapeutic dosing range for enalapril is 5–20 mg daily, given as a single dose or two divided doses. For most patients the usual initial daily dosage of captopril is 25 mg tid, with most patients having a satisfactory clinical improvement at 50 or 100 mg tid.

It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I, including the compound of Formula II, are used according to the present invention.

The example which follows is intended in no way to limit the scope of this invention, but is provided to illustrate how to use the compounds of this invention. Many other embodiments will be readily apparent to those skilled in the art.

EXPERIMENTAL

Mortality Studies in CHF Patients

Summary

To determine if β-adrenergic blockade might inhibit the deleterious effects of the sympathetic nervous system on survival in heart failure (CHF), 1052 patients with CHF were prospectively enrolled into a multicenter trial program, in which patients were randomly assigned (double-blind) to 6–12 months' treatment with placebo (PBO) or carvedilol (CRV),. After a common screening period, patients with class II–IV CHF (see next paragraph for the definitions of the classification of CHF) and an ejection fraction ≦0.35 were assigned to one of four protocols based on performance on a 6-minute walk test. PBO or CRV was added to existing therapy with digoxin, diuretics and an ACE inhibitor. All-cause mortality was monitored by a prospectively constituted Data and Safety Monitoring Board (DSMB). After 25 months of enrollment, the DSMB recommended termination of the program because of a favorable effect of CRV on survival. By intention-to-treat, mortality was 8.2% in the PBO group but only 2.9% in the CRV group (P=0.0001, Cochran-Mantel-Haensel analysis). This represented a reduction in risk of death by CRV of 67% (95% CI: 42% to 81%). The treatment effect was similar in patients with class II and class III–IV symptoms. Mortality was reduced in class II patients from 5.9% to 1.9%, a 68% reduction (95% CI: 20% to 97%) [P=0.015,], and in class III–IV patients from 11.0% to 4.2%, a 67% reduction (95% CI: 30% to 84%), [P=0.004, log-rank]. Importantly, the effect of CRV was similar in ischemic heart disease (risk reduced by 67%, P=0.003) and in non-ischemic dilated cardiomyopathy (risk reduced by 67%, P=0.014). In conclusion, the addition of CRV to conventional therapy is associated with a substantial (67%) reduction in the mortality of patients with chronic CHF. The treatment effect is seen across a broad range of severity and etiology of disease.

As used herein, by "Class II CHF" is meant patients with cardiac disease resulting in slight or moderate limitation of physical activity. They are comfortable at rest. Ordinary physical activity results in fatigue, palpitations, dyspnea, or anginal pain. By "Class III CHF" is meant patients with cardiac disease resulting in marked limitations of physical activity. They are comfortable at rest. Less than ordinary physical activity results in fatigue, palpitations, dyspnea, or anginal pain. By "Class IV CHF" is meant patients with cardiac disease resulting in inability to carry on any physical activity without discomfort, symptoms or cardiac insufficiency, or of the anginal syndrome. By "less than ordinary physical actvity" is meant climbing one flight of stairs, or walking two hundred yards.

Design of Study

Patients on background therapy with diuretics, ACE inhibitors and/or digoxin were stratified on the basis of baseline submaximal exercise performance, into one of four trials:

study 220, a dose response study in moderate (NYHA II–IV) CHF with exercise testing as a primary endpoint study 221, a dose titration study in moderate (NYHA II–IV) CHF with exercise testing as a primary endpoint study 239, a dose titration study in severe (NYHA III–IV) CHF with quality of life as a primary endpoint study 240, a dose titration study in mild (NYHA II–III) CHF with progression of CHF as a primary endpoint Sixty-four centers in the US participated in the trial program. All sites conducted protocols 239 and 240, while 33 performed protocol 220 and 31 performed protocol 221.

Although each trial had its own individual objectives, the overall program objective defined prospectively was evaluation of all-cause mortality. Based upon a projected enrollment of 1100 patients, the program had 90% power to detect a 50% reduction in mortality (two-sided) between carvedilol and placebo, assuming a mortality rate in the placebo group of 12% over the duration of the trials (α=0.05).

Randomization was preceded by a screening and challenge period common to the four protocols The purpose of the screening period was to qualify patients for study entry, obtain reproducible baseline measurements, and stratify patients into the appropriate trial based on submaximal exercise testing. During the challenge period, patients received low-dose open-label carvedilol (6.25 mg b.i.d.) for two weeks. Patients unable to tolerate this dose did not proceed to randomization. Patients tolerating low-dose carvedilol were then randomized to blinded medication (carvedilol or placebo) with the dose titrated over several weeks in the range of 6.25 to 50 mg b.i.d. (or equivalent level of placebo). The maintenance phase of each study ranged from six to 12 months, after which patients had the option of receiving open-label carvedilol in an extension study.

Results

The analysis presented below corresponds to the data set on which the DSMB made the recommendation to terminate the trials. Included in this intent-to-treat analysis are all patients enrolled in the U.S. trials as of Jan. 20, 1995; 624 receiving carvedilol and 356 placebo. An analysis of baseline patient characteristics (Table 1) shows good balance between the randomized groups.

TABLE 1

US Carvedilol Heart Failure Trials - Baseline Characteristics

| Characteristic | Placebo (n = 356) | Carvedilol (n = 624) |
|---|---|---|
| Age, mean ± SD (years) | 59.9 ± 11.7 | 58.8 ± 11.8 |
| Sex (% men) | 62% | 62% |
| Etiology (% ischemic) | 43% | 40% |
| Severity of CHF | | |
| Class II | 41% | 41% |
| Class III–IV | 40% | 39% |
| Unknown | 19% | 20% |
| LV ejection fraction, mean ± SD | 0.22 ± 0.07 | 0.23 ± 0.08 |
| 6 Minute walk (m ± SD) | 373 ± 88 | 379 ± 81 |
| Blood pressure (mmHg) | 115/73 | 115/73 |
| Heart rate (bpm ± SD) | 85 ± 13 | 86 ± 13 |

The overall mortality results for the program are shown in Table 2. All deaths that occurred during the intent-to-treat period are included. Treatment with carvedilol resulted in a 67% reduction in the risk of all-cause mortality. Analysis of mortality by certain baseline characteristics shows this to be a broad effect regardless of severity or etiology of CHF. The effect was uniform in patients with mild heart failure or moderate to severe heart failure. Similarly, the mortality reduction was equivalent in patients with ischemic or non-ischemic heart failure.

TABLE 2

Evaluation of Mortality in US Carvedilol CHF Studies

| | Carvedilol | Placebo | Risk Reduction (95% CI) | p value* |
|---|---|---|---|---|
| All Cause Mortality | 18/624 (2.9%) | 29/356 (8.2%) | 67% (42–81) | <0.0001 |
| Class II CHF | 7/361 (1.9%) | 12/202 (5.9%) | 68% (20–97) | 0.015 |
| Class III–IV CHF | 11/263 (4.2%) | 17/154 (11.0%) | 66% (30–84) | 0.004 |
| Ischemic Etiology | 10/311 (3.2%) | 16/178 (8.9%) | 67% (32–85) | 0.003 |

TABLE 2-continued

Evaluation of Mortality in US Carvedilol CHF Studies

| | Carvedilol | Placebo | Risk Reduction (95% CI) | p value* |
|---|---|---|---|---|
| Non-Ischemic Etiology | 8/313 (2.5%) | 13/178 (7.3%) | 67% (20–86) | 0.014 |

*Cochran-Mantel-Haensel Analysis

Conclusion

The U.S. Phase III trials were prospectively designed to evaluate the effects of carvedilol on the wellbeing and survival of patients with congestive heart failure. Twenty-five months after the program was initiated, the independent Data and Safety Monitoring Board recommended that the trials be terminated because of a 67% reduction in all-cause mortality. This effect was independent of the underlying severity or etiology of heart failure.

The foregoing is illustrative of the use of the compounds of this invention. This invention, however, is not limited to the precise embodiment described herein, but encompasses all modifications within the scope of the claims which follow.

What is claimed is:

1. A method of decreasing mortality caused by congestive heart failure in a patient in need thereof which comprises administering a therapeutically acceptable amount of carvedilol in conjunction with one or more other therapeutic agents, said agents being selected from the group consisting of an angiotensin converting enzyme inhibitor (ACE), a diuretic, and digoxin.

2. A method according to claim 1 which comprises administering carvedilol in a dosage range of from about 3.125 to about 50 mg given twice daily.

3. A method according to claim 1 which comprises administering carvedilol in a maintenance dose of about 25 mg given twice daily.

4. A method according to claim 1 which comprises administering carvedilol in a maintenance dose of between about 25 mg and about 50 mg given twice daily to patients whose weight exceeds about 85 kg.

5. A method according to claim 1 which comprises administering carvedilol in a maintenance dose of about 50 mg given twice daily in patients whose weight exceed about 85 kg.

6. A method according to claim 1 wherein said ACE inhibitor is captopril, lisinopril, or enalapril, or any pharmaceutically acceptable salt thereof.

7. A method according to claim 1 wherein said diuretic is hydrochlorothiazide or furosemide, or any pharmaceutically acceptable salt thereof.

* * * * *